(12) United States Patent  
Moore et al.

(10) Patent No.: US 7,950,297 B2
(45) Date of Patent: May 31, 2011

(54) NONDESTRUCTIVE INSPECTION HEADS FOR COMPONENTS HAVING LIMITED SURROUNDING SPACE

(75) Inventors: Charles Crawford Moore, Hibbs, PA (US); Michael Charles Moore, Hibbs, PA (US); Michael F. Fair, Oakmont, PA (US); James A. Bauer, Gibsonia, PA (US); Michael J. Metala, Murrysville, PA (US)

(73) Assignee: Siemens Energy, Inc., Orlando, FL (US)

( * ) Notice: Subject to any disclaimer, the term of this patent is extended or adjusted under 35 U.S.C. 154(b) by 270 days.

(21) Appl. No.: 11/776,187

(22) Filed: Jul. 11, 2007

(65) Prior Publication Data

US 2009/0126493 A1 May 21, 2009

Related U.S. Application Data

(63) Continuation of application No. 11/087,029, filed on Mar. 22, 2005.

(51) Int. Cl.
*G01M 19/00* (2006.01)

(52) U.S. Cl. .......................................... 73/865.8; 73/660
(58) Field of Classification Search ..................... 73/618, 73/644, 619, 620, 865.8
See application file for complete search history.

(56) References Cited

U.S. PATENT DOCUMENTS

| | | | |
|---|---|---|---|
| 4,094,306 A * | 6/1978 | Kossoff ........................... 73/607 |
| 4,196,049 A * | 4/1980 | Burns et al. ................... 376/249 |
| 4,304,133 A | 12/1981 | Feamster, III | |
| 5,781,007 A | 7/1998 | Partika et al. | |
| 5,948,985 A * | 9/1999 | Brautigan et al. .............. 73/622 |
| 6,637,266 B1 | 10/2003 | Froom | |
| 6,792,809 B1 | 9/2004 | Moore | |
| 2006/0081051 A1* | 4/2006 | Kessler et al. .................. 73/618 |
| 2007/0289385 A1* | 12/2007 | Kiuchi ............................ 73/627 |

* cited by examiner

*Primary Examiner* — Hezron Williams
*Assistant Examiner* — Nashmiya Fayyaz

(57) ABSTRACT

An inspection head where non-destructive inspection is structured to fit into narrow spaces, and to accurately and repeatably move an inspection probe along a surface to be inspected. Movement of the inspection head along an X, Y, Z, Θ, and Φ-axis is precisely controlled by individual drive mechanisms.

15 Claims, 16 Drawing Sheets

NONDESTRUCTIVE INSPECTION HEADS FOR COMPONENTS HAVING LIMITED SURROUNDING SPACE

CROSS REFERENCE TO RELATED APPLICATIONS

This application is a continuation of patent application Ser. No. 11/087,029, filed on Mar. 22, 2005.

BACKGROUND OF THE INVENTION

1. Field of the Invention

The present invention relates to non-destructive inspection of turbine components. More specifically, the invention provides inspection heads for positioning sensing elements on the surface of turbine rotor discs on either a fully assembled rotor or on discs that have been removed from the rotor in a controlled, repeatable manner.

2. Description of the Related Art

The blades of steam turbines are attached to discs and are subjected to significant stress due to the heat, pressure, and vibrations within their operating environments. It is therefore necessary to periodically inspect these discs for surface cracking, internal cracking, and pitting at the blade attachment area and the rotor attachment area, known as the disc bore. If such inspections locate indications of defects beginning to form that are not sufficient to take the disc out of service, it is desirable to ensure that later inspections focus on locations within the discs where the indications were found in the previous inspection.

Turbine discs are presently inspected using sensing elements such as ultrasonic probes and eddy current probes, the operation of which is well known in the art. Presently used probes are hand held, thereby limiting the positional accuracy of the inspection, and the repeatability with which the probes may be positioned.

Accordingly, there is a need for a means of accurately and repeatably positioning an inspection probe in a desired location with respect to a turbine disc. There is an additional need for such probes to fit within the small space available between discs within a typical turbine rotor assembly, thereby avoiding a need to remove the discs from the turbine for inspection.

SUMMARY OF THE INVENTION

The present invention provides a non-destructive inspection head that is particularly useful for inspecting the discs of turbines, and particularly the high stress areas, such as the blade attachment area and the disc bore area (where the disc is attached to the rotor using a "shrink fit" process for steam turbines.

For purposes of this description, the X-axis is defined as an axis substantially horizontal and substantially parallel to a disc being inspected. The Y-axis is defined as an axis that is substantially vertical, and also substantially parallel to a disc being inspected. The Z-axis is defined as an axis that is substantially horizontal, and substantially perpendicular to a disc being inspected. The Θ-axis is defined by rotation about the Z-axis. Lastly, the Φ-axis is defined by rotation around the X-axis.

The invention is structured to place an inspection probe, for example, an ultrasonic probe or an eddy current probe, adjacent to or against a disc to be inspected, while the disc remains mounted to a rotor. The turbine blades may or may not be attached to the disc during the inspection. The probe may be raised between the discs, and adjacent to the disc to be inspected, by presently available devices. As it is currently designed, one probe and head assembly is positioned on either side of the disc to be inspected. This provides a complete inspection without moving the base unit. Once the inspection head is properly positioned, the head itself is structured for movement along at least some of the X axis, Y axis, Z axis, Θ-axis and Φ-axis. Movement along each of these axes is controlled by a separate drive mechanism, so that the probe may move independently along any axis, or along more than one axis, as necessary to properly position the probe. The Θ-drive and consequentially the probe are free floating in a semi-spherical area atop the Z-drive, which allows for proper contact of the face of the probe to the disc over the various ranges of disc geometry and probe contact face contours.

If an ultrasound probe is used, a delivery/recirculation system for an ultrasonic coupling medium, for example, water, may also be provided. The delivery/recirculation system is figuratively illustrated in FIG. 17 as 137 and 139, respectively. The system is structured to dispense water between the propad and the component to be inspected, thereby providing effective ultrasonic coupling between the probe and the component. A catch basin 139 is located below the component, for catching the water so that it may be recirculated throughout the inspection process.

The inspection heads may be configured specifically to inspect specific discs on a turbine rotor assembly. For example, a linear drive head providing for movement along only the X and Y axes may be utilized for inspections near the blade attachment region, where the surfaces may be inspected along a straight line, and where the lack of Z and Θ drive mechanisms enables the inspection head to be smaller, better fitting within tight spaces. An arc drive head having an X axis drive and a Φ-axis drive may be utilized to inspect discs having a curved geometry. A standard head, having X-axis, Y-axis, Z-axis, and Θ-axis drives may be utilized to scan disc in the bore region, where the disc contacts the rotor, and is particularly useful for inspecting regions of turbine discs from the blade attachment area to the disc bore regions. Lastly, a low clearance head having X-axis, Y-axis, Z-axis, and Θ-axis drives, but with a more limited range of motion along the X-axis than the standard head, may be utilized where the minimum gap between discs is less than that which will accommodate a standard head. The use of an inspection head having precisely controlled positioning means ensures that the inspection head may be located accurately and repeatably where inspections are desired. For example, if an indication was found in a specific location in a prior inspection, but the indication was not sufficient to take the disc out of service, the inspection head may be accurately directed to the location where the indication appeared during a subsequent inspection.

Accordingly, it is an object of the present invention to provide an inspection head capable of accurately and repeatably positioning a non-destructive inspection probe against a component to be inspected.

It is another object of the invention to provide an inspection head having independently and precisely controlled drive systems for each axis of movement.

It is a further object of the invention to provide an inspection head that includes or omits specific drive mechanisms and specific directions, permitting construction of an inspection head that may fit within a narrow space in a desired location, while still providing the necessary range of motion to complete an inspection.

It is another object of the invention to provide an inspection head that may be utilized with one or two inspection probes.

It is a further object of the invention to provide an inspection head whose range of motion and precise control of positioning enable both straight on and angled directional inspections, thereby permitting an indication detected by a straight on inspection to be more precisely located using the angled inspection.

It is a further object of the invention to provide an inspection head that may be precisely positioned so that indications may be precisely located during pitch catch ultrasonic inspections.

It is a further object of the invention to provide an inspection head that may be used interchangeably with a wide variety of non-destructive inspection probes, for example, single ultrasonic, double ultrasonic, phased array ultrasonic, or eddy currents.

These and other objects of the invention will become more apparent through the following description and drawings.

BRIEF DESCRIPTION OF THE DRAWINGS

Like reference characters denote like elements throughout the drawings.

DETAILED DESCRIPTION

The present invention provides an inspection head for delivering non-destructive inspection probes to locations having limited spaces for such probes, for example, between adjacent discs of a turbine rotor assembly for inspection of the surfaces of those discs.

Figure 1:
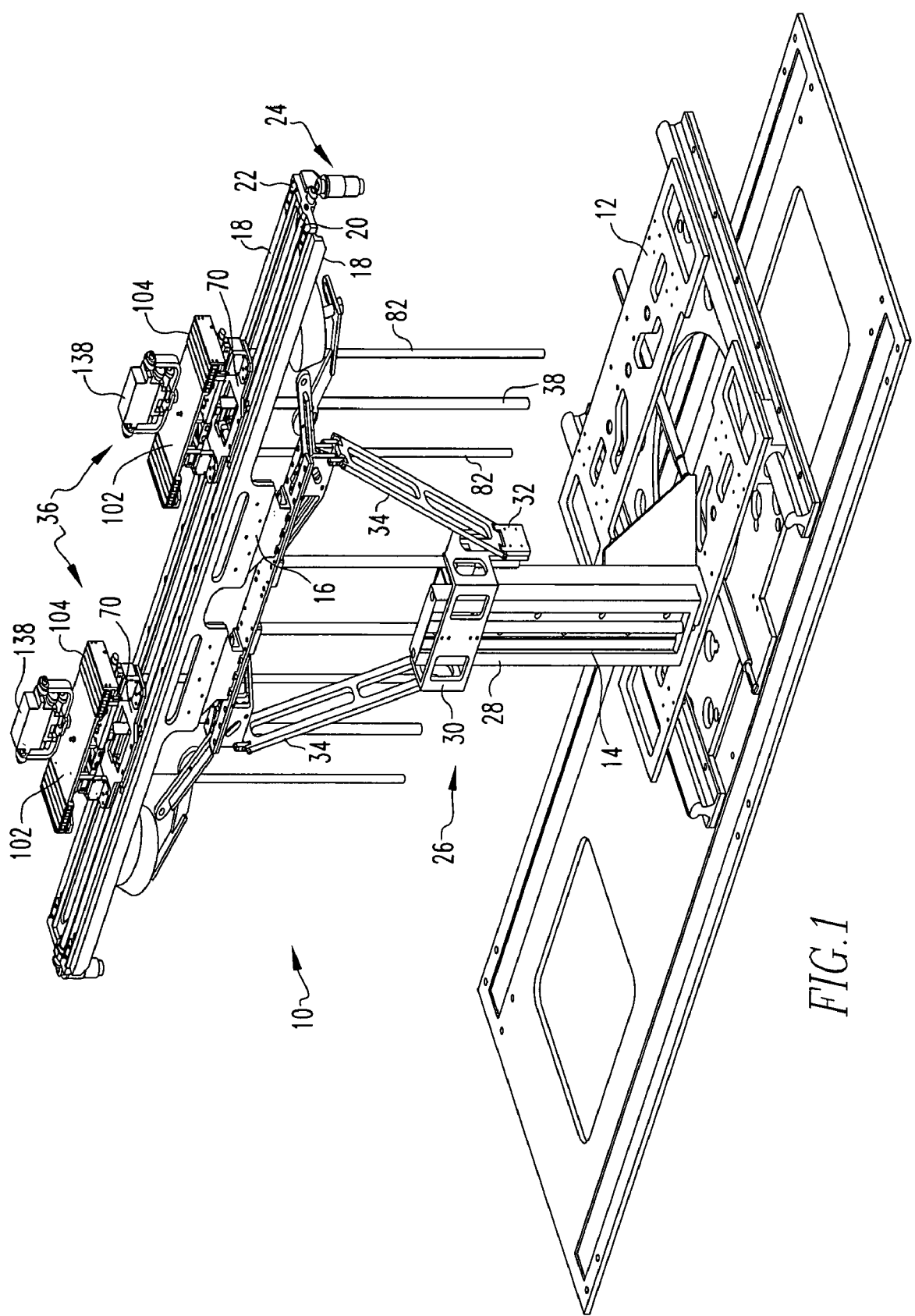
FIG. 1 is an isometric back view of a standard inspection head according to the present invention, illustrating two inspection probes thereon.
Figure 2:
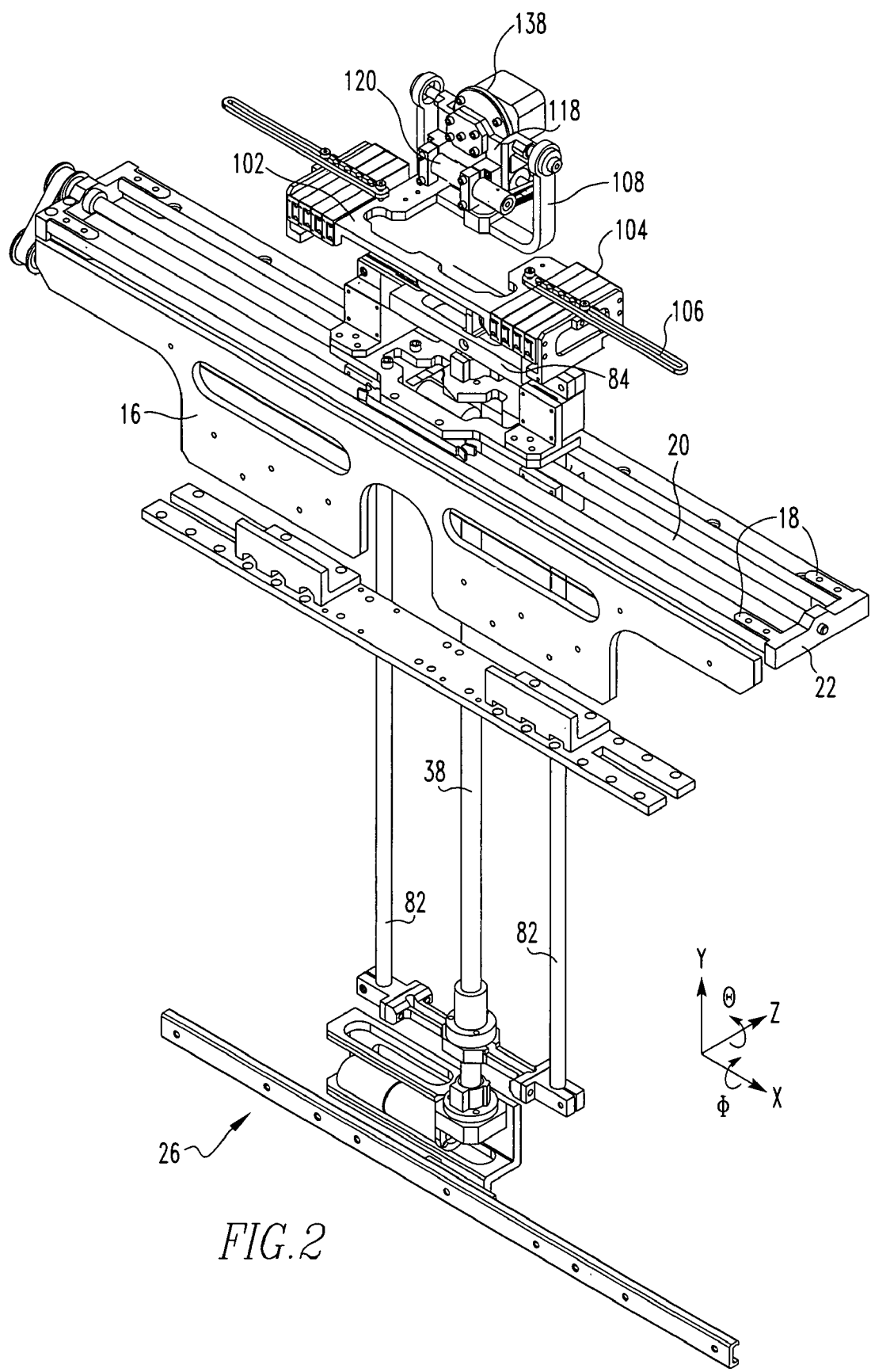
FIG. 2 is an isometric back view of a standard inspection head according to the present invention, illustrating a single inspection probe therein.

Referring to FIGS. 1-6, the first embodiment of the inspection head is illustrated, hereinafter called a standard head 10. Referring to FIGS. 1-2, the standard head 10 includes a base 12 (partially shown) structured for mounting on a presently available apparatus for raising the inspection head between adjacent discs. Although such devices are presently available, they will be briefly described below. A stand 14 extends upward from the base 12. The stand 14 terminates in a rail support plate 16. The rail support plate 16 supports a pair of rails 18 on either side of a drive screw 20, with an endcap 22 on either end of the assembly. The drive screw 20 is rotably secured between the endcaps 22, with an X-axis drive mechanism 24, which will be described in greater detail below, operatively connected to one end of the drive screw 20.

The stand 14 further includes a Y-axis drive mechanism 26, including a fixed vertical rail 28 having a bracket 30 secured at its top end. A pair of sliders 32 are slidably mounted on the rail 28, with an arm 34 extending upward from each slider 32 to the rail support plate 16. In addition to the movement of the rail support plate 16 with respect to the base 12, the individual probe assemblies 36 may move vertically with respect to the rail support plate 16. A motor driven screw rail 38, the operation of which will be described below, provides for vertical positioning adjustment of each probe assembly 36.

Figure 3:
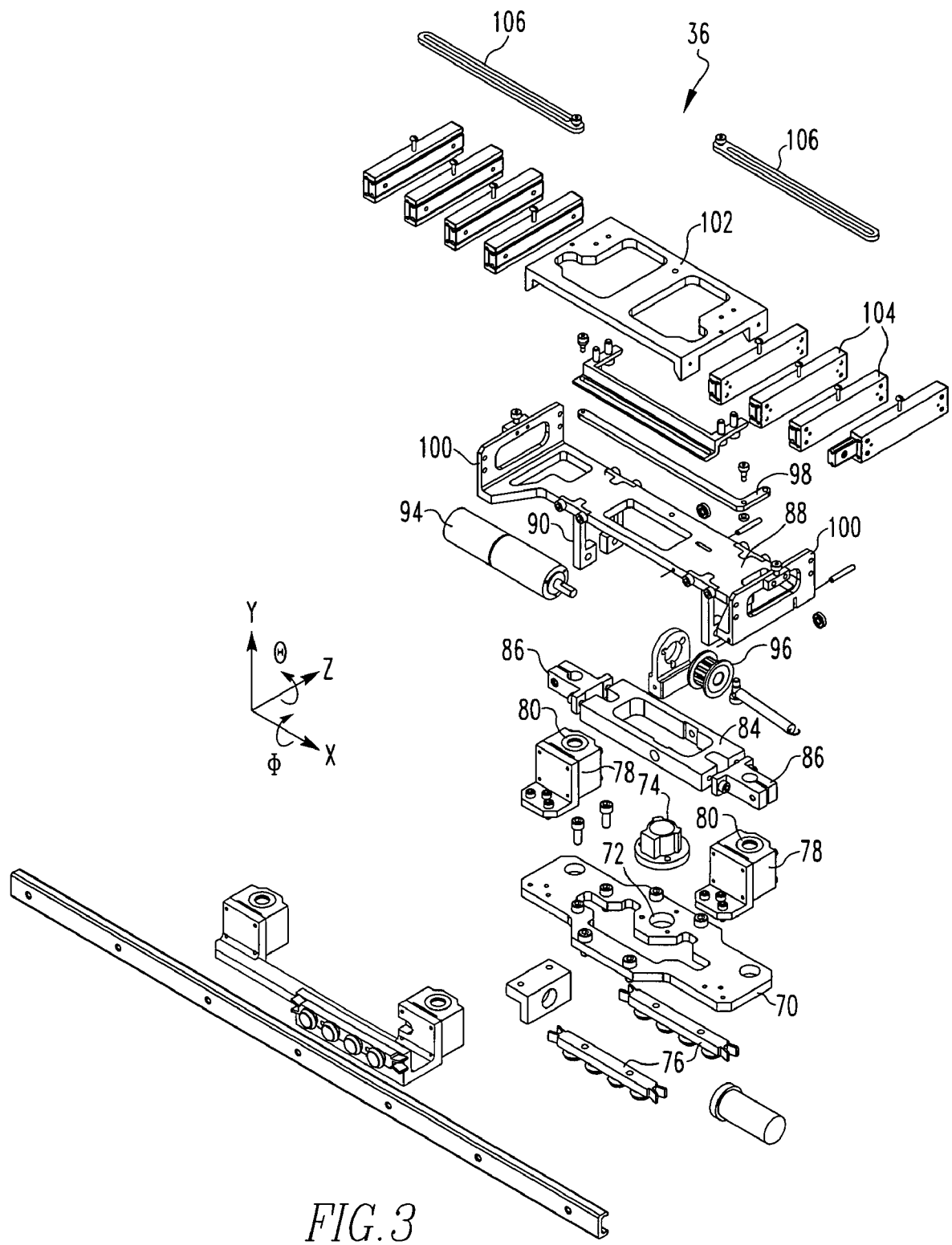
FIG. 3 is an isometric, partially exploded back view of the upper portion of an inspection head according to FIG. 2.
Figure 4:
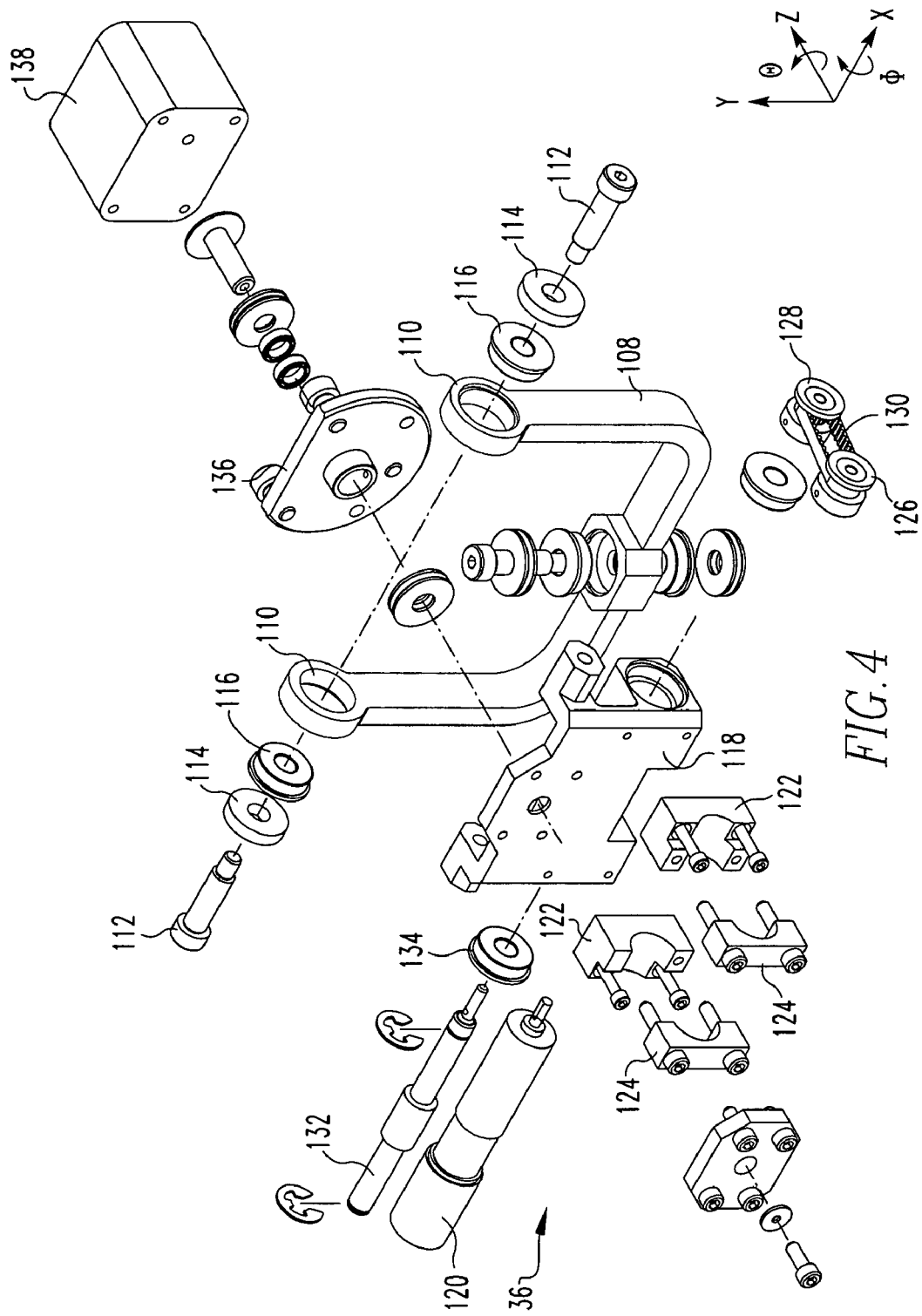
FIG. 4 is an isometric, partially exploded back view of an inspection probe assembly according to the present invention.
Figure 5:
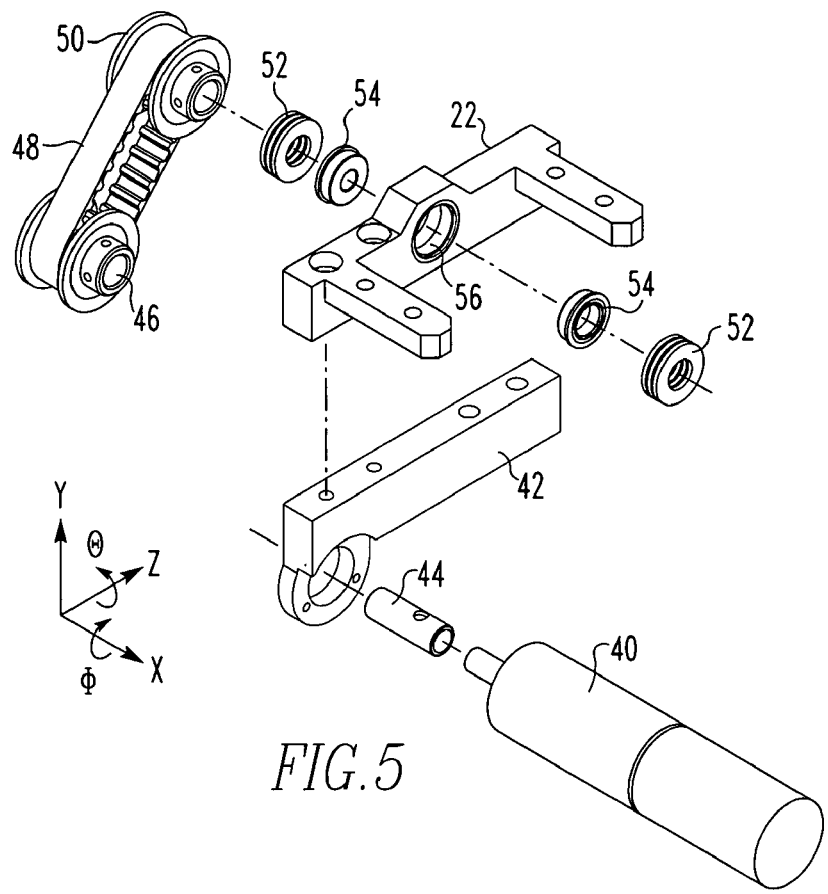
FIG. 5 is an isometric, partially exploded back view of an X-axis drive mechanism for use with the inspection head of FIG. 2.

The standard head 10 is illustrated in more detail in FIGS. 3-6. Referring specifically to FIGS. 2 and 5, the drive screw 20 is controlled by the X-axis drive motor 40. The X-axis drive motor 40 is mounted to a motor mount 42 which is secured below one of the two end caps 22. The motor 40 is connected through the bushing 44 to the pulley 46, which drives the drive belt 48, thereby turning the pulley 50. The pulley 50 is connected to the drive screw 20 through the thrust bearings 52 and ball bearings 54, thereby facilitating rotation within the hole 56 defined within the end cap 22.

Figure 6:
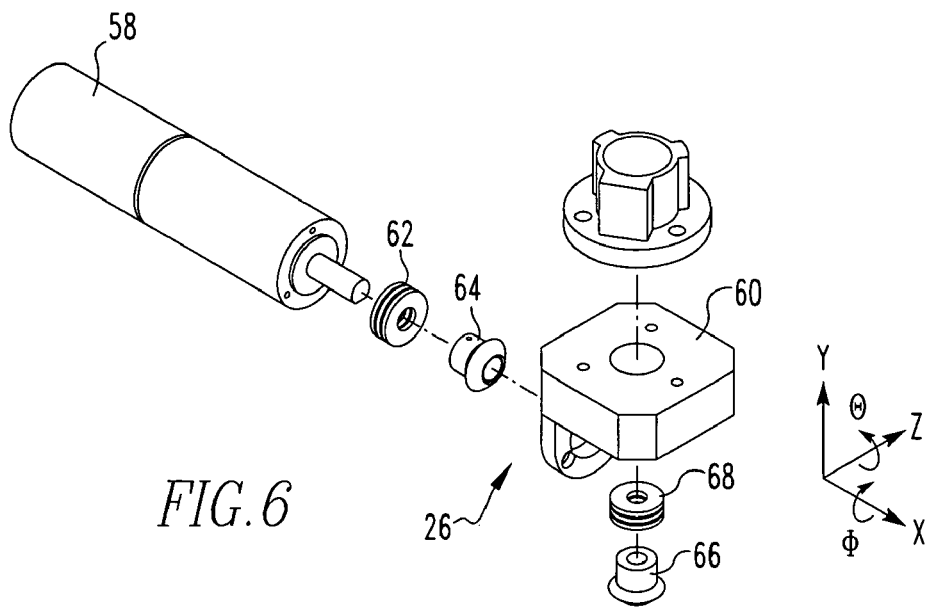
FIG. 6 is a partially exploded, isometric back view of a Y-axis drive mechanism for use with an inspection head of FIG. 2.

Referring to FIGS. 2 and 6, the Y-axis drive mechanism 26 is illustrated in more detail. The Y-axis motor 58 is secured to the motor mount 60. The Y-axis motor 58 is operatively connected to the Y-axis drive screw 38 through the thrust bearing 62, miter gear 64, miter gear 66, and thrust bearing 68, with the interaction of the two miter gears 64, 66 inverting the horizontal rotation imparted by the motor 58 to the vertical rotation necessary to rotate the drive screw 38.

Referring to FIGS. 2-4, a probe assembly 36 is illustrated. The bottom of the probe assembly 36 includes a trolley plate 70, which is threadedly engaged by the Y-axis drive screw 38 passing through the aperture 72 defined within the trolley plate 70. The screw rail end 74 is located directly above the aperture 72. A pair of trolleys 76 are secured to the lower side of the trolley plate 70, and are structured to engage the rails 18, thereby permitting the probe assembly 36 to slide along the rails 18. A pair of pillow block assemblies 78 are disposed on either side of the trolley plate 70, and define holes 80 therethrough, with the holes 80 being structured to receive a guide shaft 82 on either side of the Y-axis drive screw 38. This portion of the probe assembly 36 remains adjacent to the rails 18, with the remainder of the probe assembly 36, described below, being structured for movement along the Y-axis as controlled by the motor 58.

A shaft hangar 84 forms the lower portion of the movable part of the probe assembly 36. Each end 86 of the shaft hangar 84 is structured to clamp around the guide shaft 82. A bracket 88 is disposed above the shaft hangar 84 motor mounts 90, 92 extend downward from the bracket 88 and upward from the shaft hangar 84, respectively, and secure a Z-axis motor 94 therein. The Z-axis motor 94 turns the pulley 96, which is operatively connected to the Z-drive arm 98 that is partially secured above the bracket 88. The bracket 88 further defines a pair of upward extending end flanges 100, with a mount 102 centered thereon, and a plurality of roller slides 104 between each side of the mount 102 and the corresponding flange 100. An alignment plate 106 is pivotally mounted to each side of the mount 102, and pivotally and slidably mounted across the roller slides 104 on that side and the upward extending flange 100 of the bracket 88. Actuation of the Z-axis motor 94 thereby causes the Z-drive arm 98 to move the mount 102 along the Z-axis, with the roller slides 104 ensuring that the movement imparted by the Z-axis motor 94 remains substantially along the Z-axis. Movement of the mount 102 in the opposite direction is achieved by spring pressure on the Z-drive arm 98.

A U-shaped bracket 108 is pivotally mounted on the mount 102, with the ends of the U-shape extending upward. The upper ends of the U-shape define a pair of holes 110, structured to receive a screw 112 passing through a thrust bearing 114 and ball bearing 116, into either side of a probe plate 118, thereby pivotally securing the probe plate 118 within the bracket 108. A Θ-axis motor 120 is secured to the back of the probe plate 118 by the brackets 122 and clamps 124. The Θ-axis motor 120 is operatively connected to the pulley 126, which is operatively connected to the pulley 128 through the belt 130. The pulley 128 is in turn connected to the worm gear shaft 132, mounted on the front of the probe plate 118, via the bearing 134. The worm gear shaft 132 engages the worm gear 136, to which the sensor 138 has been secured. The sensor 138 may be an ultrasound sensor, eddy current sensor, or other non-destructive inspection sensor. The sensor 138 may thereby be rotated around the Θ-axis by the Θ-axis motor 120 to change the angle at which a disc is inspected.

Figure 7:
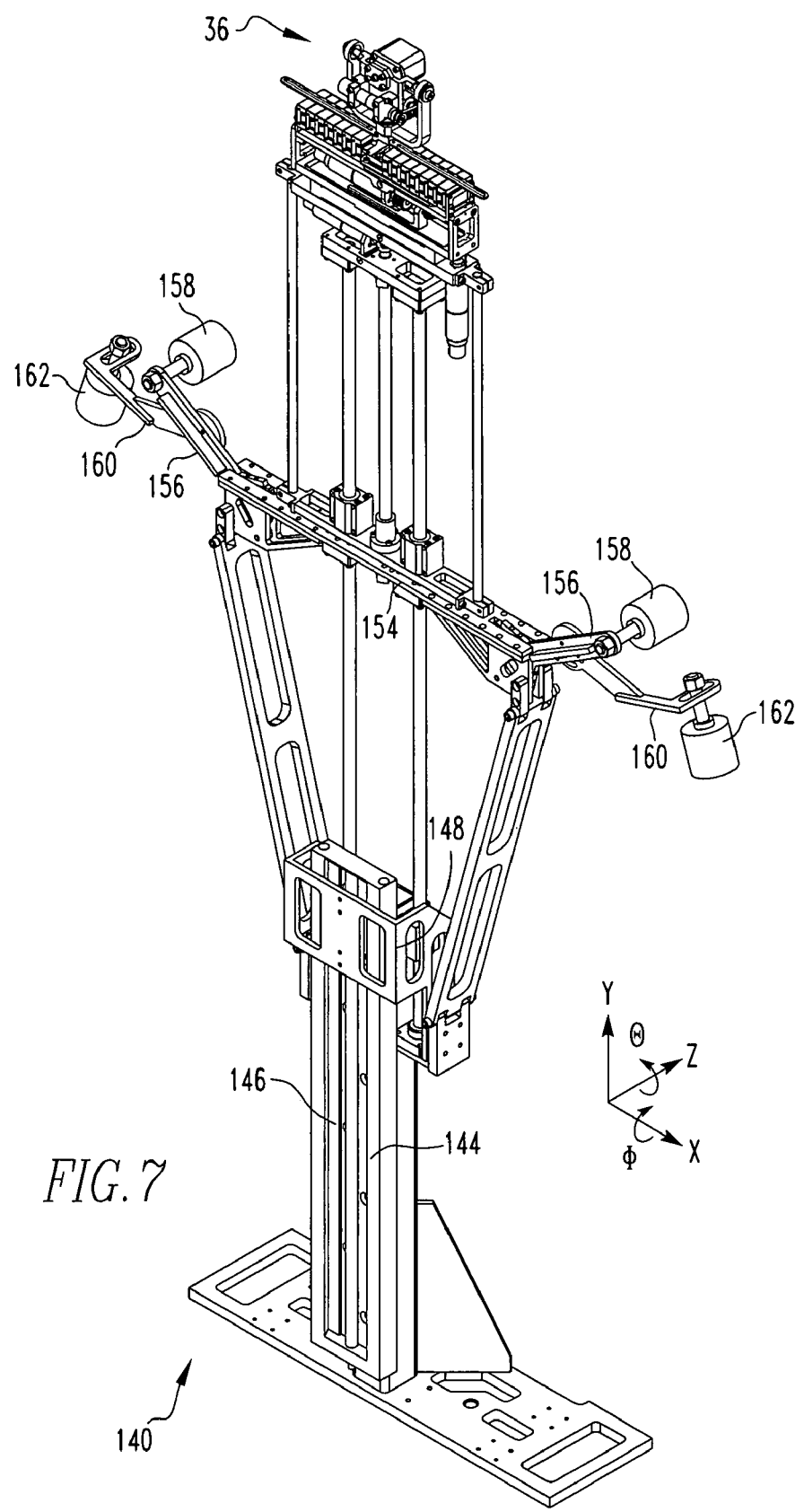
FIG. 7 is an isometric, back view of a low clearance inspection head according to the present invention.
Figure 8:
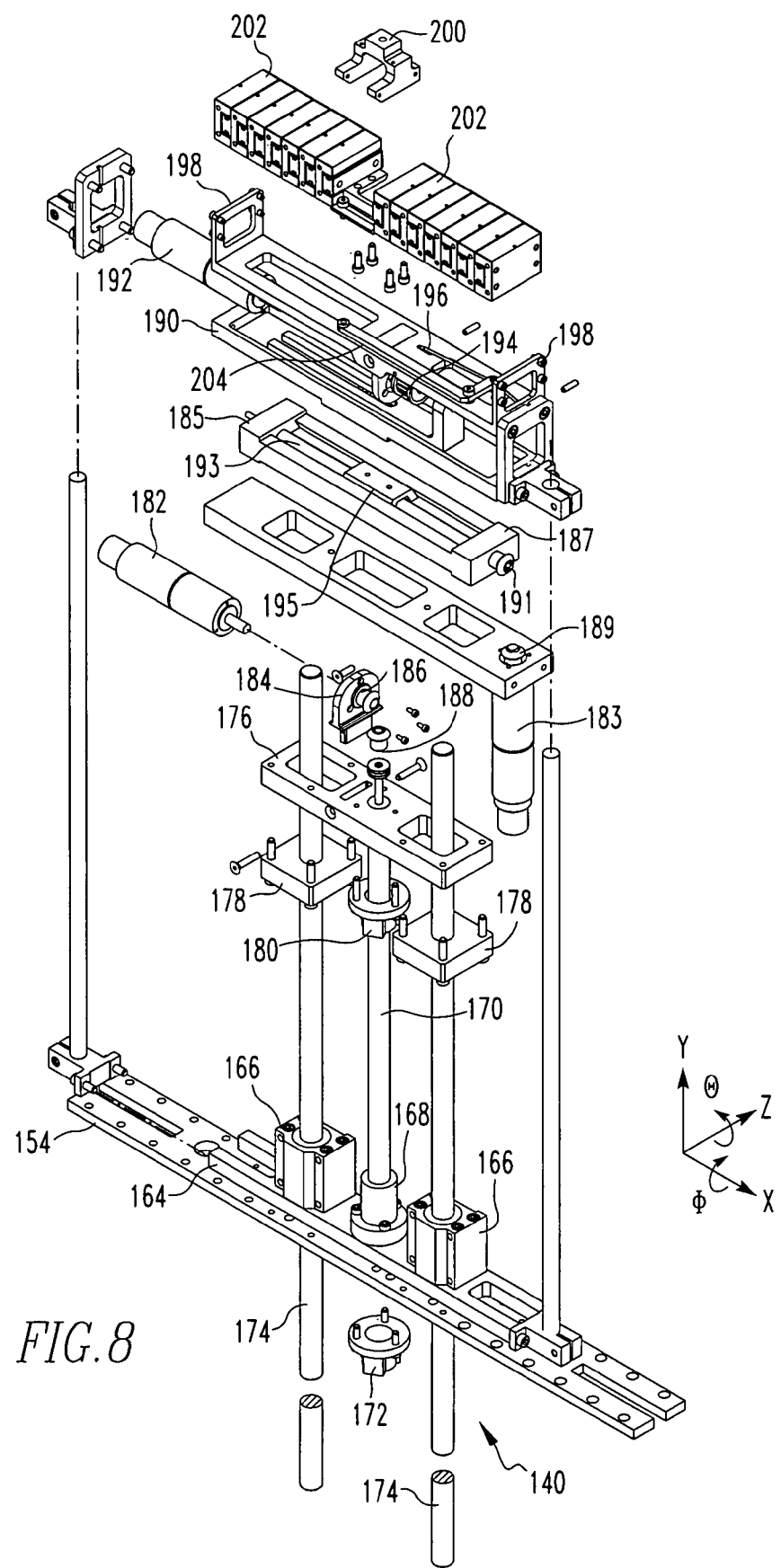
FIG. 8 is an isometric, partially exploded back view of an upper portion of a low clearance inspection head according to FIG. 7.
Figure 9:
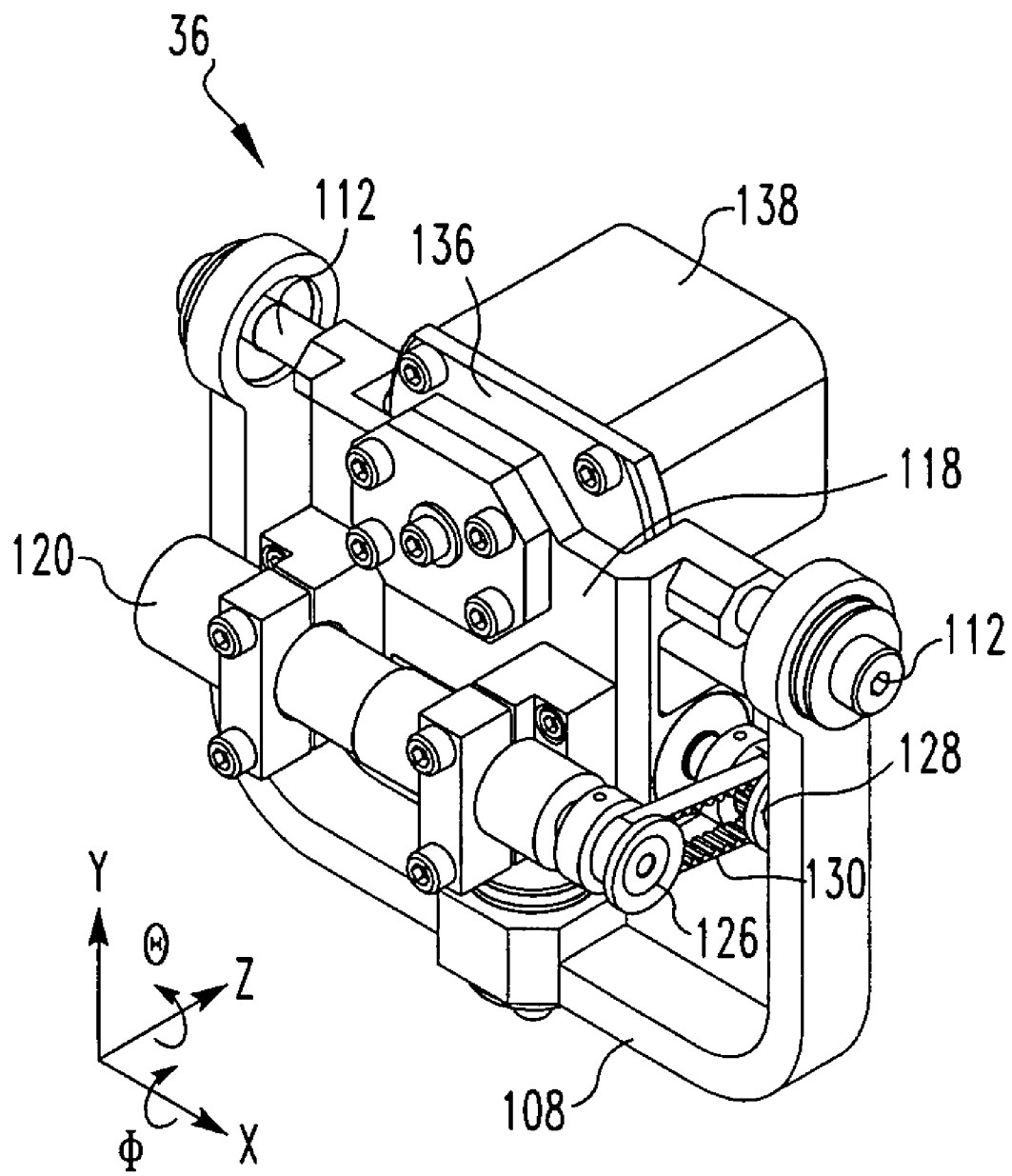
FIG. 9 is an isometric back view of an inspection probe utilized with the inspection head of FIG. 7.

Referring to FIGS. 7-9, a low clearance head 140 is illustrated. The low clearance head 140 is similar to the standard head 10 in many respects. The low clearance head 140 includes the base 142 structured for mounting on a presently available apparatus for raising the inspection head between adjacent discs. A stand 144 extends upward from the base 142. The stand 144 includes a fixed vertical rail 146 having a bracket 148 secured at its top end. A pair of sliders 150 are slidably mounted on the rail 144, with an arm 152 extending upward from each slider 150 to either side of a top plate 154. A pair of arms 156 extends outward from the top plate 154, and may include rollers 158 pivotally secured to their ends. A second pair of arms 160 extends outward from the arms 156, and include a pair of rollers 162 pivotally secured to their ends.

A Y-base plate 164 may be disposed on top of the top plate 154. A pair of bolsters 166 are disposed atop either side of the Y-base plate 164, with a thrust bearing 168 located between the top bolsters, on top of the Y-base plate. A Y-axis drive screw 170 extends upward through the Y-base plate 164 and thrust bearing 168, terminating at its lower end with the end cap 172. A pair of guide rods 174 are disposed on either side of the Y-axis drive screw 170, passing through the Y-base plate 164 and top bolsters 166. The above described portion of the low clearance head 140 remains stationary during movement in the Y-direction, while the following portion will move along the Y-axis.

A Y-drive base 176 is disposed at the top end of the guide rods 174 and Y-axis drive screw 170. A support block 178 may be disposed below the Y-drive base, surrounding and providing additional support for each of the guide rods 174. An endcap 180 surrounds and provides additional support for the Y-axis drive screw 170. A Y-axis motor 182 is mounted on top of the Y-drive base 176, and may be secured there by the motor bracket 184. The Y-axis motor 182 is operatively connected to the drive screw 170 through the interaction of the miter gear 186, connected to the Y-axis motor 182, and the miter gear 188, connected to the Y-axis drive screw 170.

An X-axis motor 183 is mounted on a mounting plate 185, at the top of the guide rods 174. A dovetail slide 187 is mounted on the mounting plate 185, being operatively connected to the X-axis motor 183 by the interaction of the miter gear 189, attached to the motor 183, and the miter gear 191, attached to the leadscrew 193 of the dovetail slide 187. The slider 195, threadedly connected to the leadscrew 193, is connected to the Z-drive base 190.

A Z-drive base 190 is disposed above the Y-drive base 176, and supports a Z-drive motor 192 thereon. The motor 192 is operatively connected to a pulley 194. A slide mount plate 196 is disposed above the Z-drive base 190 and Z-drive motor 192. The slide mount plate 196 defines a pair of upwardly extending flanges 198 at each end. The head mount plate 200 is centered on the slide mount plate 196, with a plurality of roller slides 202 located between each side of the head mount plate 200 and the corresponding upward flange 198. The roller slides 202 are all interconnected to the directly adjacent roller slides 202, in a manner that permits only linear sliding motions in a Z direction with respect to each other. A Z-drive arm 204 is pivotally secured to the top surface of the slide mount plate 196, and is operatively connected to the pulley 194 and the head mount plate 200. Actuation of the Z-axis motor 182 thereby moves the pulley 194, thereby causing the Z-drive arm 204 to move the head mount plate 200 along the Z-axis, with the roller slides 202 limiting the movement of the head mount plate 200 to within the Z-axis. A probe assembly 36, identical to the probe assembly 36 described above, is mounted on top of the head mount plate 200.

Figure 10:
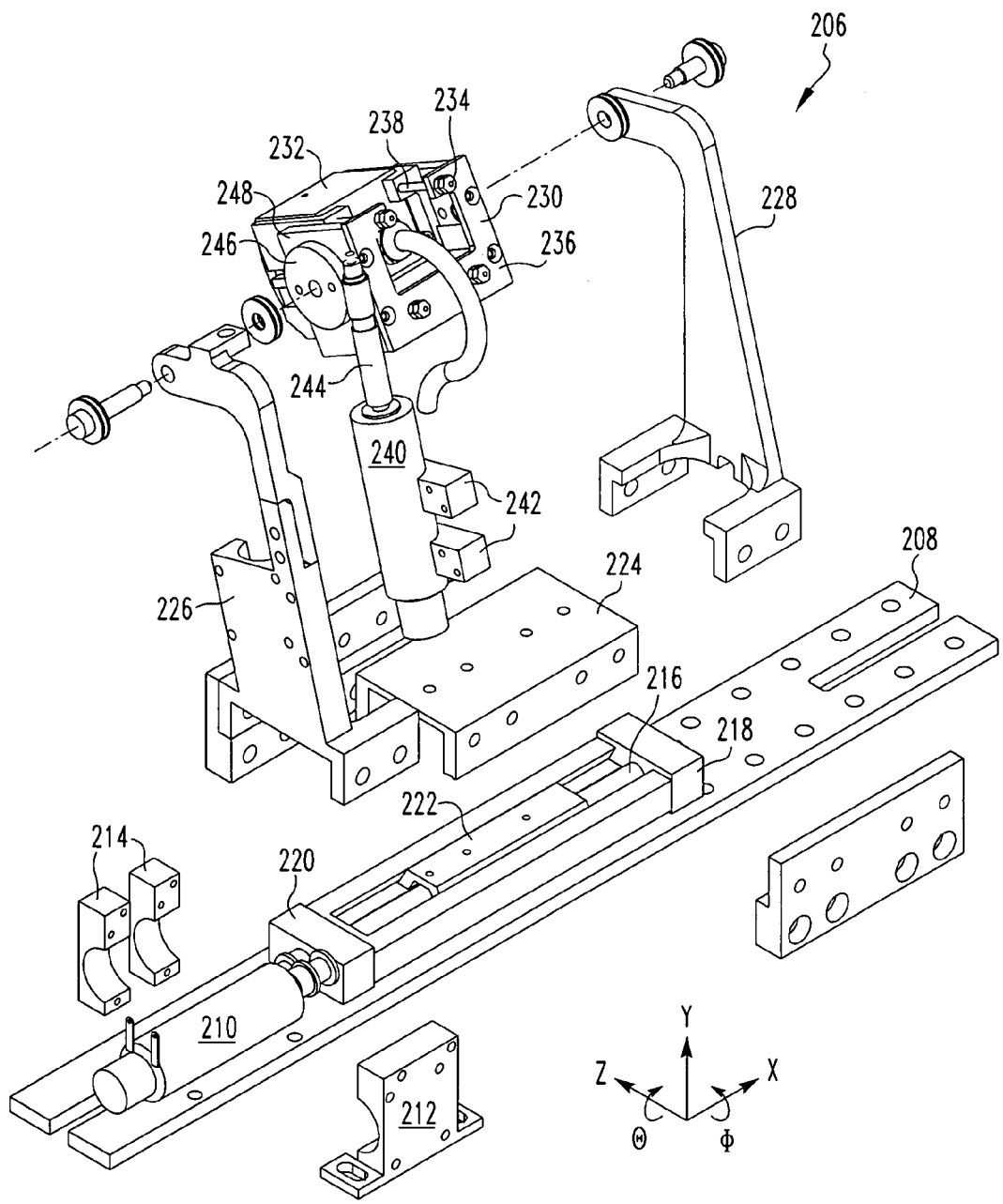
FIG. 10 is an isometric, partially exploded back view of upper portion of an arc drive inspection head according to the present invention.

Referring to FIG. 10, an arc drive head 206 is illustrated. The arc drive head 206 sits atop a base plate 208, which is similar to the top plate 154, and which may be used to attach the arc drive head 206 to a base 12 and stand 14, similar to those used for other inspection heads. The base plate 208 has an X-axis motor 210 secured thereto by the motor bracket portions 212, 214. The motor 210 turns a drive screw 216 mounted between a pair of end blocks 218, 220. A slider 222 is threadably secured to the drive screw 216, and is rigidly attached to a slide base 224. A pair of curved support arms 226, 228 extend upward from the slide base 224, pivotally securing a probe frame 230 between their top ends. A probe 232 is secured within the probe frame 230 by a plurality of screws 234 passing through the back 236 of the probe frame 230, and then threadably engaging the probe 232. Each of the screws 232 has a spring disposed thereon, thereby biasing the probe 232 away from the back 236 of the probe frame 230. Rotation of the probe frame 230 about the Φ-axis is controlled by the Φ-axis motor 240, which is mounted on the probe support arm 226 by the motor bracket 242. The motor 240 is operatively connected to a worm gearshaft 244, extending upward therefrom, and which engages the worm gear 246 mounted on the side 248 of the probe housing 230.

Figure 11:
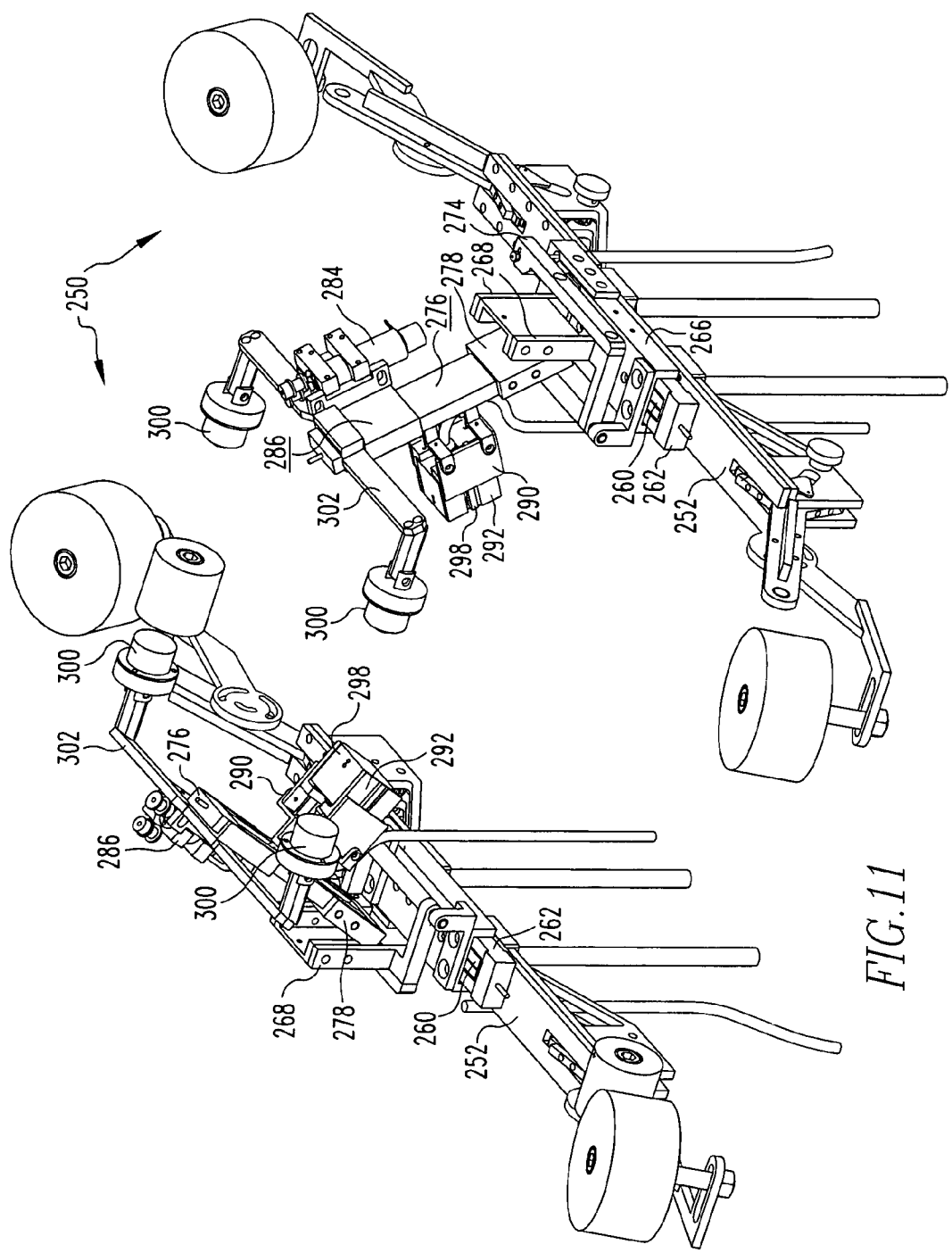
FIG. 11 is an isometric view of a pair of linear drive inspection heads according to the present invention.
Figure 12:
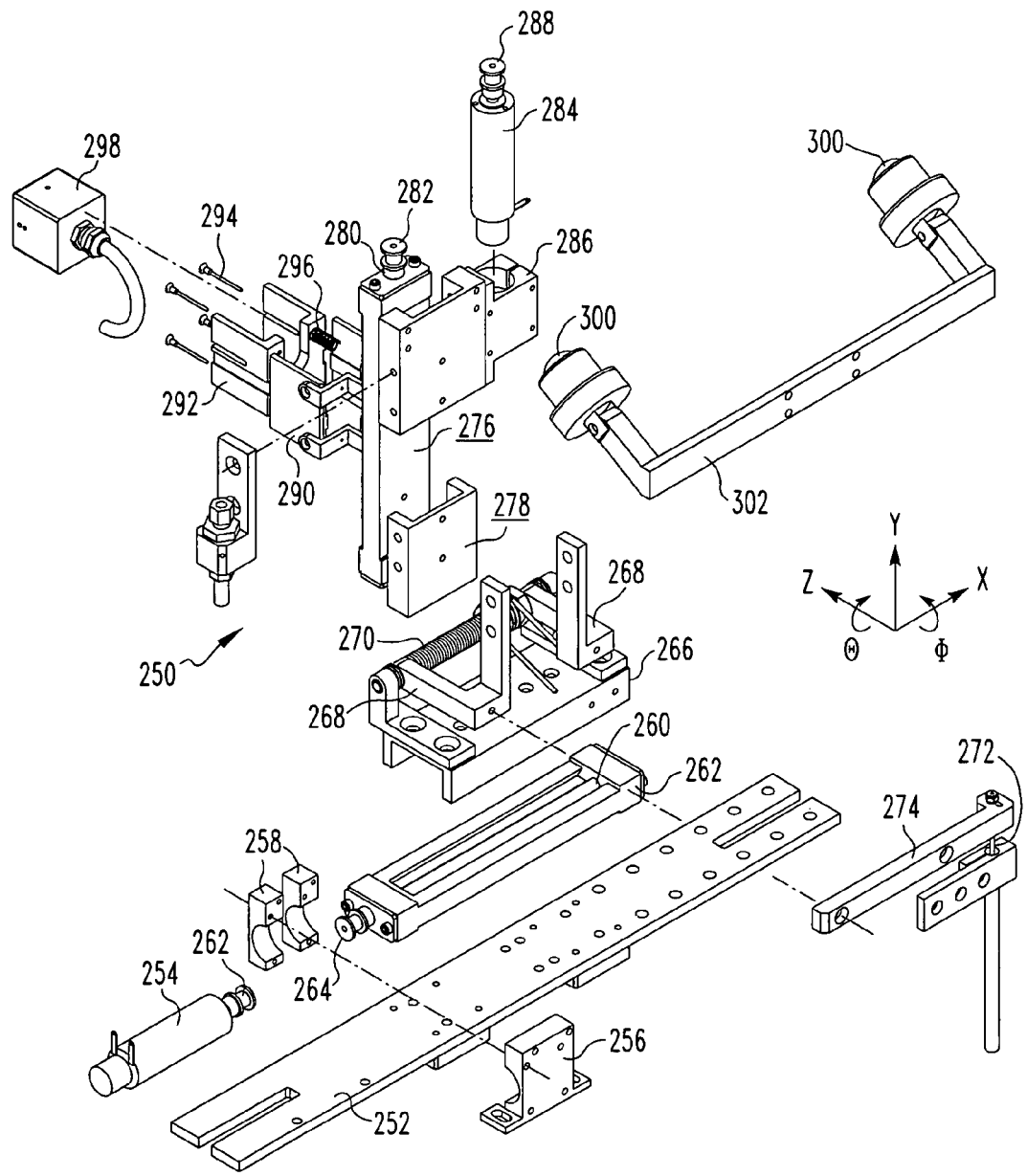
FIG. 12 is an isometric, partially exploded back view of an upper portion of a linear drive inspection head according to the present invention.

Referring to FIGS. 11-12, a linear drive head 250 is illustrated. The linear drive head 250 includes a base plate 252 that is similar to the base plate 208. An X-axis drive motor 254 is secured to the base plate between the brackets 256, 258. The motor 254 is operatively connected to a drive screw 260 housed within a slide 262, mounted on the base plate 252. A pulley 262 connected to the motor 254 is connected by a belt to a pulley 264 connected to the X-axis drive screw 260. A slide base 266 is threadably secured to the X-axis drive screw 260, so that the movement of the slide base 266 and the X-axis direction is controlled by the motor 254.

A pair of generally L-shaped arms 268 are secured to the slide base 266, and a slider 276 is secured between the L-shaped arms 268, with the bracket 278 therebetween. The bracket 278 is biased away from the slide base 266 by the spring 270. A cable 272 secured at one end to a bracket 274 which is itself secured to the bracket 278 may be used to pull the bracket 278 towards the slide base 266. A Y-axis drive screw 280 is secured within the slider 276, and has a pulley 282 at one end. A Y-axis motor 284 is secured to the top of the slider 276 by the bracket 286, and is operatively connected to the pulley 288. A belt between the pulleys 282, 288 thereby permits the Y-axis motor 284 to control the Y-axis drive screw 280. An outer probe frame 290 is threadably secured to the Y-axis drive screw 280. An inner probe frame 292 is secured within the outer probe frame 290 by a plurality of screws 294, each of which has a spring 296 disposed thereon between the outer probe frame 290 and inner probe frame 292, thereby biasing the inner probe frame 292 away from the outer probe frame 290. A probe 298 is housed within the inner probe frame 292. As with all other inspection heads, on the probe 298 may be an ultrasonic inspection probe, an eddy current inspection probe, or other non-destructive inspection probe. A pair of rollers 300 are disposed near the top of the linear drive head 250, and in the illustrated embodiment are secured to the arm 302 secured to the bracket 286.

Figure 13:
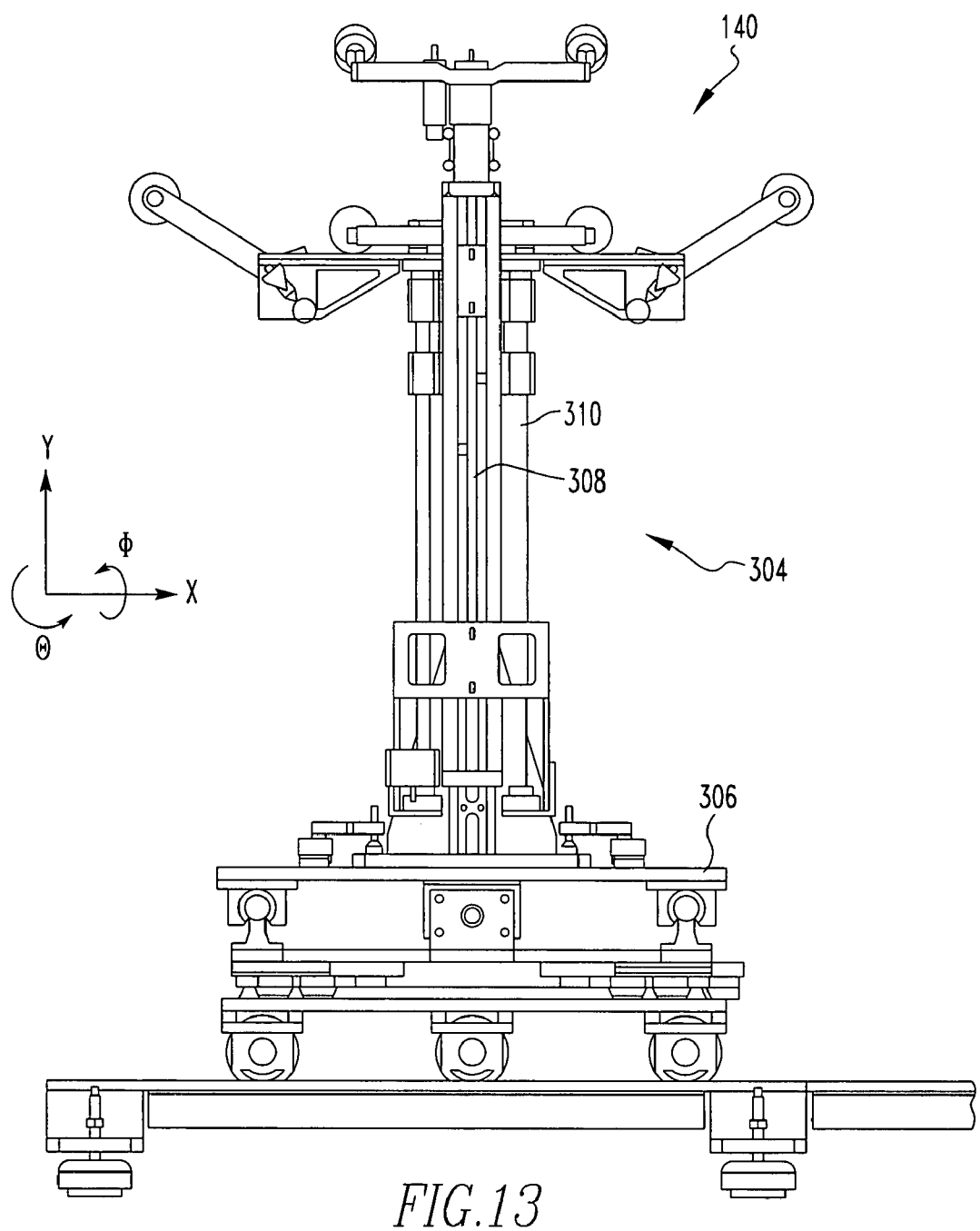
FIG. 13 is a back view of an inspection head and inspection head lifting mechanism according to the present invention.
Figure 14:
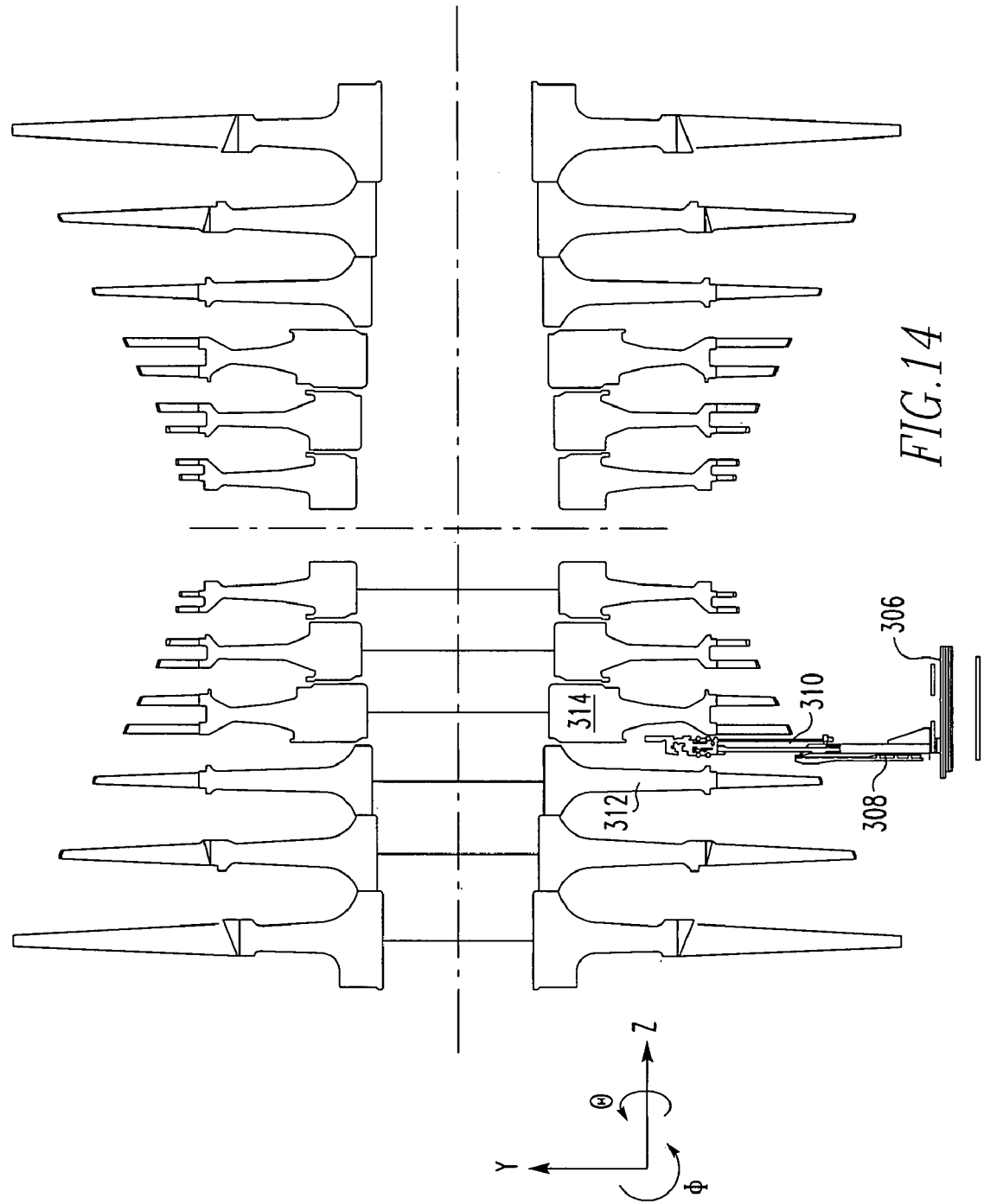
FIG. 14 is an environmental, isometric side view of an inspection head according to the present invention being utilized to perform an inspection on the discs of a fully assembled steam turbine rotor.
Figure 15:
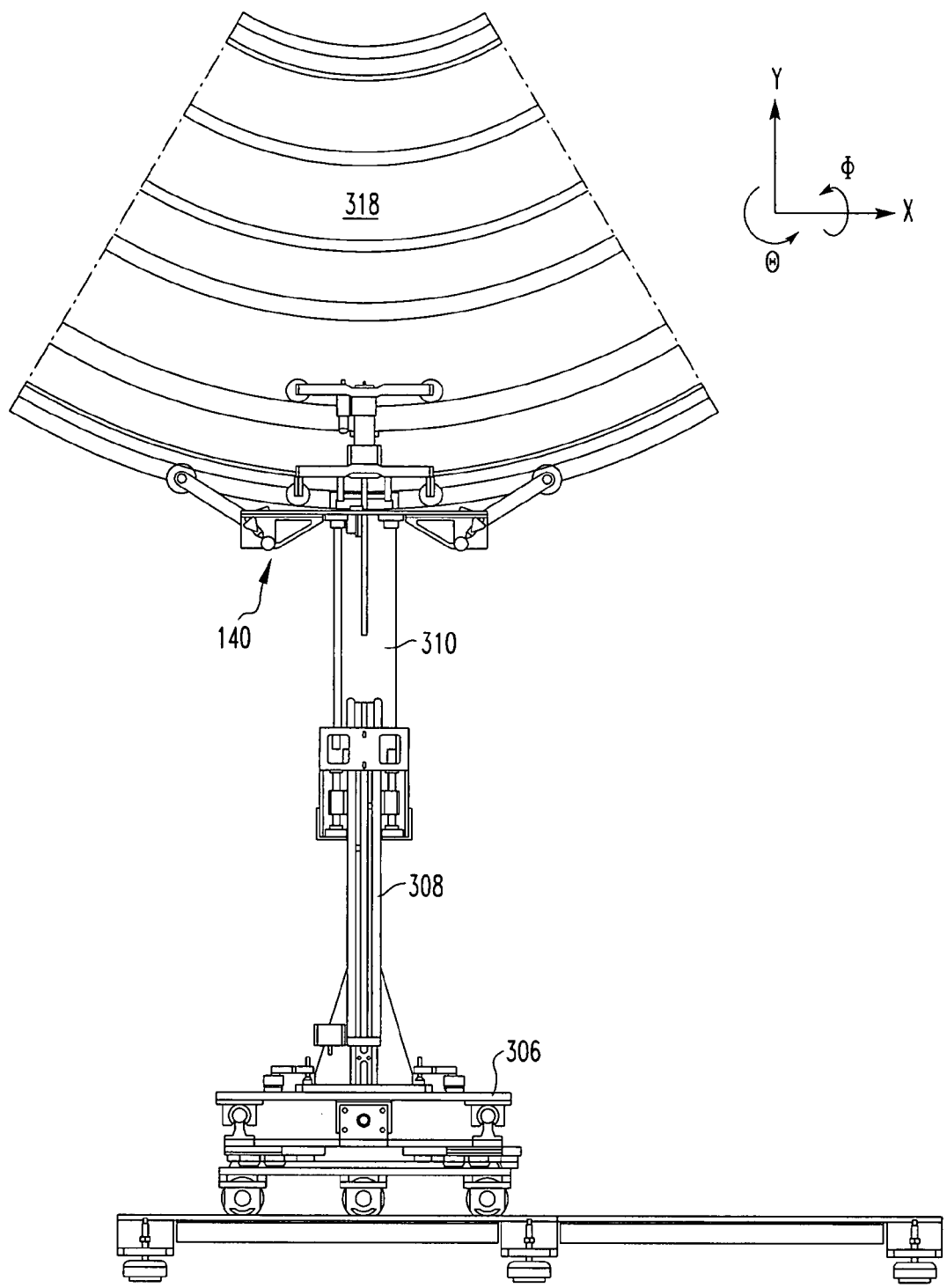
FIG. 15 is a back view of an inspection head and inspection head lift mechanism according to the present invention, being utilized to perform an inspection.
Figure 16:
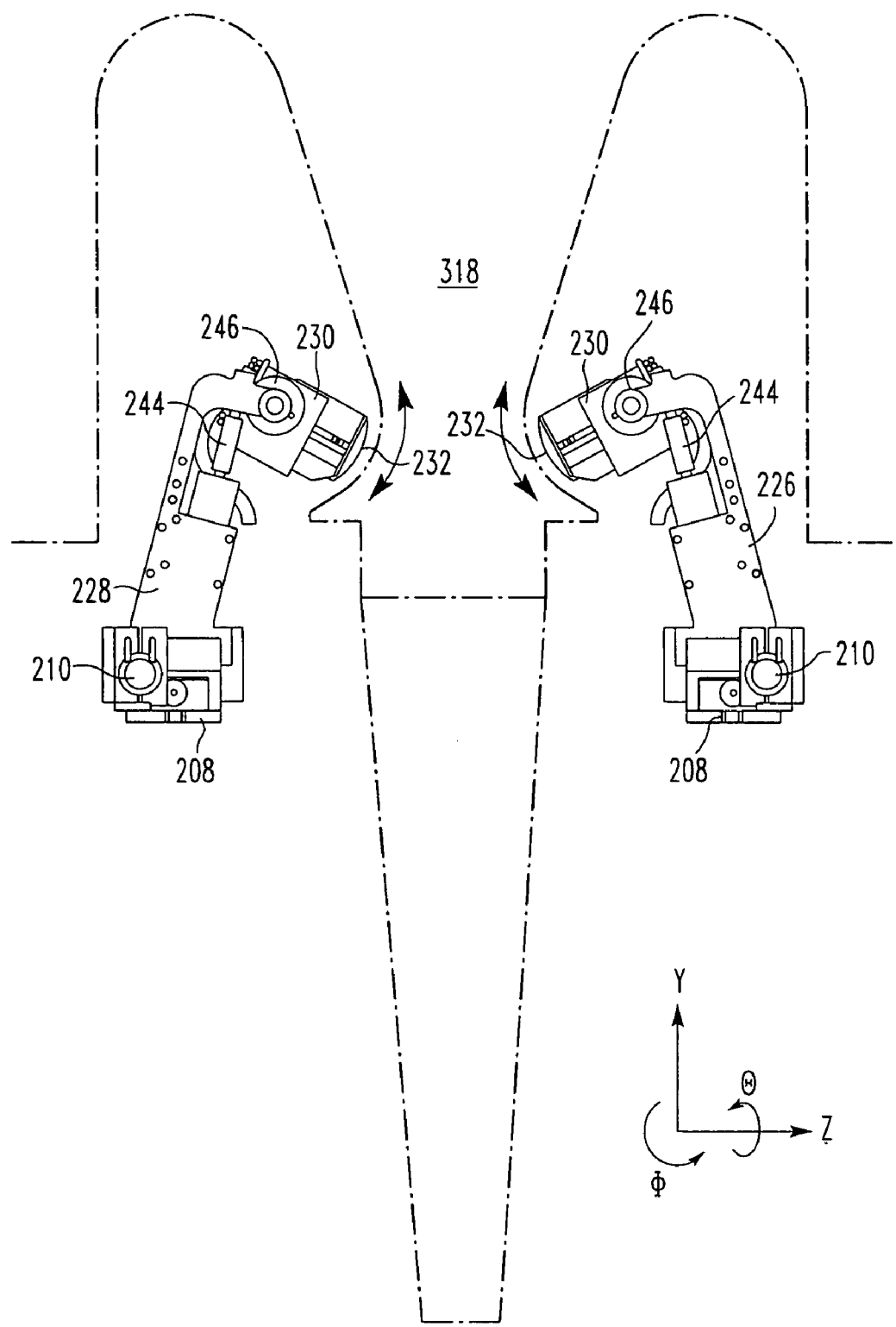
FIG. 16 is a side view of a pair of arc drive inspection heads performing an inspection on a disc of a steam turbine rotor assembly.

Referring to FIGS. 13-15, a probe insertion apparatus 304 is illustrated. The probe insertion apparatus 304 includes a base 306 having a stationary telescoping member 308 extending upward therefrom. A sliding telescoping member 310 fits around the stationary telescoping member 308. Any of several inspection heads may be secured to the top of the sliding telescoping member 310. The sliding telescoping member may be caused to move up and down with respect to the stationary telescoping member using any of several means that are well known in the art, for example, manually, through the use of hydraulic cylinders, through the use of an electric motor driving an appropriate pulley and/or gear system, etc. Because such systems are well known in the prior art, they will not be described further herein. When an inspection is desired, the sliding telescoping member may be raised with respect to the stationary telescoping member from the position of FIG. 13 to the position of FIGS. 14-15, thereby locating the appropriate inspection head between a pair of turbine discs 312, 314. The inspection head may then be moved into engagement with the disc as described above. In the case of the linear drive head of FIGS. 11-12, the spring 270 is allowed to bias the arms 268 to rotate the inspection head 250 against the disc 318. In the case of the arc drive head of FIGS. 10 and 16, the Θ-axis motor 240 will be actuated to orient the probe 232 along the surface of the disc 318. In the case of the low clearance head of FIG. 15, the inspection head 140 will be moved along the X, Y, and Z-axes until it properly engages the disc 318. Depending upon the inspection to be performed, the disc may be rotated while the inspection head remains stationary, or the disc may remain stationary while the inspection head is moved along one of its axes of movements.

Figure 17:
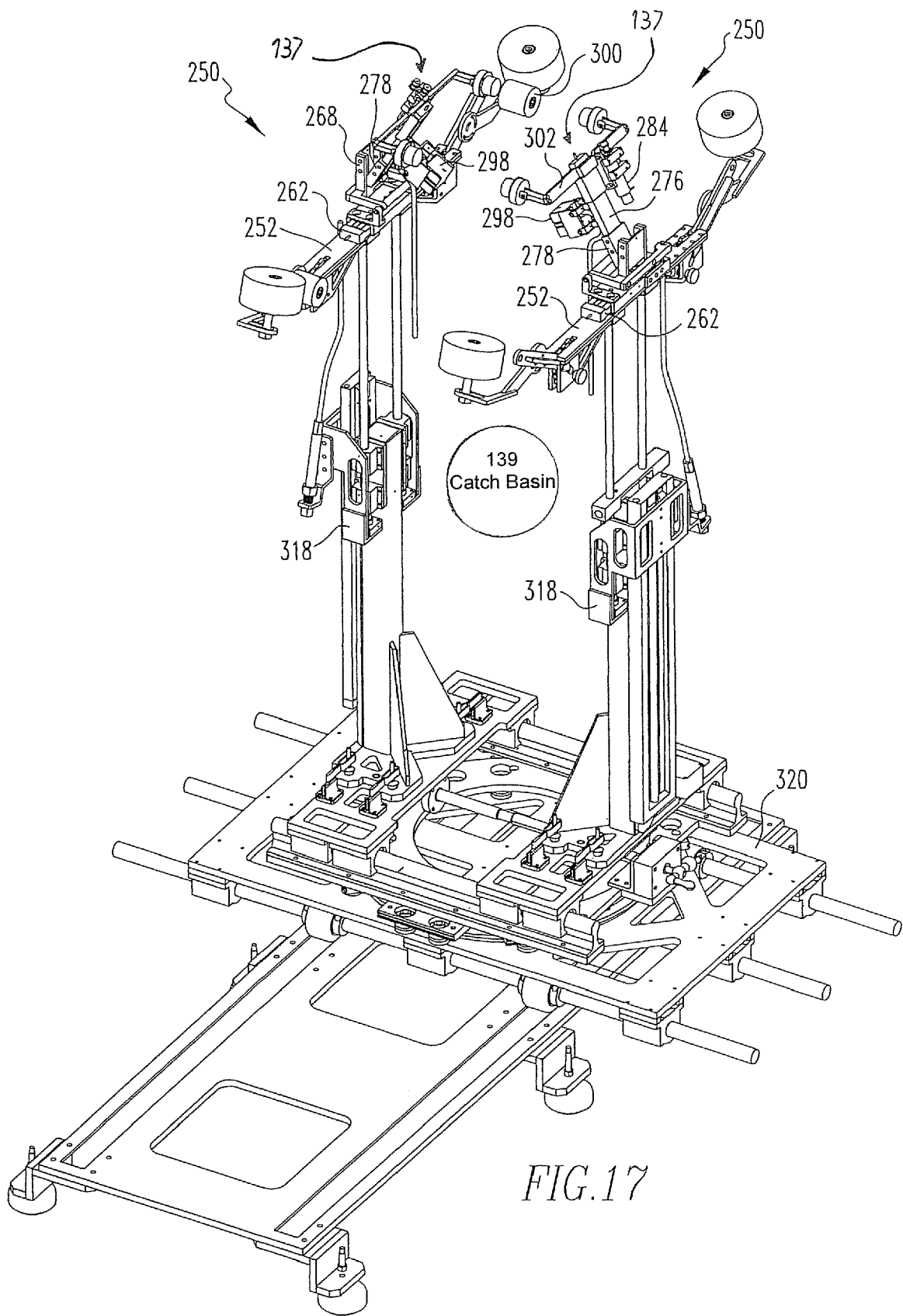
FIG. 17 is an isometric view of a pair of linear drive inspection heads according to the present invention as configured to perform an inspection on both sides of a disk simultaneously.

As another alternative, the standard head may be configured to place two probes on the same side or opposite sides of the disc. FIG. 1 illustrates a pair of inspection heads 36, each of which may move independently of the other along the X, Z, and/or Θ axis. As a further alternative, any head may be used in pairs, on opposite sides of a disc, either for pitch-catch inspection or merely to reduce the time required to perform an inspection as shown by the pair of linear drive heads 250 in FIG. 17. Each linear drive head 250 is supported by a stand 318 connected to a common base 320, so that both heads 250 may be placed adjacent to opposite sides of a disk simultaneously. In a pitch-catch inspection, which is well-known in the art of nondestructive testing, one probe transmits an ultrasonic signal that is received by the other probe.

The present invention therefore provides an inspection head capable of accurately and repeatably positioning a non-destructive inspection probe against a component to be inspected. The inspection head has independently and precisely controlled drive systems for each axis of movement, and is constructed in a manner that permits the inspection head to fit within relatively inaccessible locations. The inspection head may be utilized with either ultrasound, eddy current, or other non-destructive inspection probes, may be utilized with individual or multiple probes, and enables both straight and angled directional inspections.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A nondestructive inspection head system for the inspection of a turbine disk component on a turbine rotor assembly, comprising:
   means for raising and lowering an interchangeable inspection head along a Y-axis into a location to be inspected;
   the interchangeable inspection head configured to inspect a turbine disk component comprising;
      a Y-axis drive;
      a drive selected from the group consisting of an X-axis drive, a Θ-axis drive and a Φ-axis drive;
   a Z-axis drive,
      wherein the Z-axis drive includes a motor structured to drive the head in a first direction, and a spring structured to drive the head in an opposing direction,
      wherein a plurality of interconnected, substantially parallel slides adjacent to each other and structured to slide with respect to each other;
   an arm structured to actuate sliding motion of the slides;
   a spring structured to bias the arm in a first direction; and
   a motor-driven pulley structured to move the arm in the opposing direction;
   a sensor; and
   a coupling medium delivery/recirculation system structured to:
      dispense a coupling media between the sensor and the turbine disk, and recirculate the coupling media via a catch basin arranged below the turbine disk.

2. The inspection head system according to claim 1, further comprising a θ-axis drive.

3. The inspection head system according to claim 2, wherein the θ-axis drive includes a motor-driven belt, with the belt driving a leadscrew operatively connected to a gear that is operatively connected to the head.

4. The inspection head system according to claim 1, wherein the X-axis drive includes a lead screw actuated by a motor-driven pulley.

5. The inspection head system according to claim 1, further comprising a probe holder structured to hold a probe in a floating manner.

6. The inspection head system according to claim 1, wherein the sensor is selected from the group consisting of ultrasound and eddy current.

7. The inspection head system according to claim 6, wherein the sensor comprises a pair of ultrasonic probes.

8. The inspection head system according to claim 6, wherein the coupling media is water.

9. The inspection head system according to claim 1, further comprising at least two rollers structured to engage a surface of the component being inspected.

10. The inspection head system according to claim 5, wherein the probe is secured within a probe housing, and the probe is spring-biased away from the probe housing.

11. A nondestructive inspection head system for the inspection of a turbine disk component on a turbine rotor assembly, comprising:
 a base having a stand and rail support structured to raise and lower an interchangeable inspection head along a Y-axis into a location to be inspected of the turbine disk component;
 the interchangeable head comprising:
  an Y-axis drive operatively connected to the head;
  a drive selected from the group consisting of a X-axis drive, a θ-axis drive and a Φ-axis drive, operatively connected to the head;
  a Z-axis drive operatively connected to the head,
  wherein the Z-axis drive includes a motor structured to drive the head in a first direction, and a spring structured to drive the head in an opposing direction,
  wherein a plurality of interconnected, substantially parallel slides adjacent to each other and structured to slide with respect to each other;
  an arm structured to actuate sliding motion of the slides;
  a spring structured to bias the arm in a first direction; and
  a motor-driven pulley structured to move the arm in the opposing direction; and
  a sensor operatively connected to the X, Y or Φ-axis drive that detects defects in an inspected turbine disk component; and
 a coupling medium delivery/recirculation system structured to:
  dispense a coupling media between the sensor and the inspected turbine disk component, and
  recirculate the coupling media via a catch basin arranged below the inspected turbine disk component.

12. The inspection head system according to claim 11, wherein the inspected turbine disk component comprises an attached turbine blade.

13. The inspection head system according to claim 12, wherein the blade is a steam turbine blade.

14. The inspection head system according to claim 13, further comprising a probe connected to the head selected from the group consisting of ultrasound and eddy current.

15. The inspection head system according to claim 12, further comprising a probe holder structured to hold a probe in a floating manner, and wherein the probe is secured within a probe housing and the probe is spring-biased away from the probe housing.

* * * * *